United States Patent
Niedzwiecki et al.

(10) Patent No.: US 12,029,726 B1
(45) Date of Patent: Jul. 9, 2024

(54) COMPOSITION AND METHOD OF TREATING CONDITIONS ASSOCIATED WITH EXTRACELLULAR MATRIX DYSFUNCTION BY ADMINISTERING MICRONUTRIENT COMPOSITION

(71) Applicant: Matthias W Rath, Henderson, NV (US)

(72) Inventors: Aleksandra Niedzwiecki, Aptos, CA (US); Matthias W Rath, Aptos, CA (US); Vadim Ivanov, Castro Valley, CA (US)

(73) Assignee: Matthias W. Rath, Henderson, NV (US)

( * ) Notice: Subject to any disclaimer, the term of this patent is extended or adjusted under 35 U.S.C. 154(b) by 0 days.

(21) Appl. No.: 18/218,954

(22) Filed: Jul. 6, 2023

(51) Int. Cl.
| | |
|---|---|
| *A61K 31/375* | (2006.01) |
| *A61K 31/198* | (2006.01) |
| *A61K 31/205* | (2006.01) |
| *A61K 31/355* | (2006.01) |
| *A61K 31/401* | (2006.01) |
| *A61K 31/519* | (2006.01) |
| *A61K 31/593* | (2006.01) |
| *A61K 31/675* | (2006.01) |
| *A61K 31/7008* | (2006.01) |
| *A61K 31/737* | (2006.01) |
| *A61K 33/34* | (2006.01) |
| *A61K 36/15* | (2006.01) |
| *A61K 36/185* | (2006.01) |
| *A61K 36/324* | (2006.01) |
| *A61K 36/74* | (2006.01) |

(52) U.S. Cl.
CPC .......... *A61K 31/375* (2013.01); *A61K 31/198* (2013.01); *A61K 31/205* (2013.01); *A61K 31/355* (2013.01); *A61K 31/401* (2013.01); *A61K 31/519* (2013.01); *A61K 31/593* (2013.01); *A61K 31/675* (2013.01); *A61K 31/7008* (2013.01); *A61K 31/737* (2013.01); *A61K 33/34* (2013.01); *A61K 36/15* (2013.01); *A61K 36/185* (2013.01); *A61K 36/324* (2013.01); *A61K 36/74* (2013.01)

(58) Field of Classification Search
CPC .................................................. A61K 31/375
See application file for complete search history.

(56) References Cited

U.S. PATENT DOCUMENTS

| | | | |
|---|---|---|---|
| 10,736,872 B1 * | 8/2020 | Ivanov | A61K 31/455 |
| 2005/0053674 A1 * | 3/2005 | Niedzwiecki | A61K 36/752 |
| | | | 514/474 |
| 2011/0117207 A1 * | 5/2011 | Minatelli | A23L 33/17 |
| | | | 424/581 |

FOREIGN PATENT DOCUMENTS

| | | | | |
|---|---|---|---|---|
| EP | 2106791 A1 * | 10/2009 | ........... | A61K 31/198 |
| RU | 2376025 C1 * | 12/2009 | | |

OTHER PUBLICATIONS

Maroon et al., Natural anti-inflammatory agents for pain relief, Surg Neurol Int 2010; 1:80 published online Dec. 13, 2010 (Year: 2010).*
Soeken et al., "Safety and efficacy of S-adenosylmethionin (SAMe) for osteoarthritis", J Fam Practice, May 2002, vol. 51, No. 5, p. 425-430. (Year: 2002).*

* cited by examiner

*Primary Examiner* — Gina C Justice
(74) *Attorney, Agent, or Firm* — Geeta Kadambi; RIDDHI IP LLC

(57) ABSTRACT

A micronutrient composition is highly effective in treating joint related inflammation and reducing ECM damaging enzymes in joints. The micronutrient composition comprises of Vitamin C, Vitamin E (D-alpha tocopherol), Vitamin B6, Vitamin D3, Folic acid, L-proline, L-lysine, Copper, Betaine HCl, Chondroitin sulfate, N-acetyl-glucosamine, Pycnogenol, SAMe, Cat's claw, Boswellia serrata, Stinging nettle and Glutamine. The micronutrient composition was most effective in supporting critical cellular mechanisms important for healthy joints-increased production and deposition of important ECM components by synovial cells and chondrocytes under pro-inflammatory conditions (presence of LPS). The micronutrient composition also decreased pro-inflammatory IL-6 and decreased secretion of MMP13, the ECM damaging enzyme in joints.

10 Claims, 11 Drawing Sheets

COMPOSITION AND METHOD OF TREATING CONDITIONS ASSOCIATED WITH EXTRACELLULAR MATRIX DYSFUNCTION BY ADMINISTERING MICRONUTRIENT COMPOSITION

This application discloses method of treating chronic arthritis and maintaining joint health by administering micronutrient composition in mammal.

BACKGROUND

Pathologic conditions associated with extracellular matrix dysfunction include chronic arthritis as a commonly occurring disease affecting physical abilities and quality of life of millions of people around the word. Arthritis usually develops along with aging and also due to accumulated trauma and injury events. Pathological changes in affected joints are characterized by dramatic change in the composition of synovial cartilage and fluid. Pathological process of arthritis development involves chronic inflammation which is aggravating extracellular matrix dysfunction and arthritic manifestations. There is a need for sustained long effective treatment regimen to mitigate chronic disease such as arthritis.

SUMMARY

The instant micronutrient composition prevents, treats and delays the damage and dysfunction of connective tissue such as in arthritic process using the experimental model of cultured human chondrocytes and synovial fibroblasts in mammalian cell.

In one embodiment, in every figure the combination refers to micronutrient composition and comprises of Vitamin C. Vitamin E (D-alpha tocopherol), Vitamin B6, Vitamin D3. Folic acid, L-proline, L-lysine, Copper, Betaine HCl, Chondroitin sulfate, N-acetyl-glucosamine, Pycnogenol, SAMe. Cat's claw. Boswellia serrata. Stinging nettle and Glutamine. The respective components of the micronutrient mixture (shown in figures as combination) are in the range of Vitamin C 10 mg-50000 mg. Vitamin E (D-alpha tocopherol) 1 mcg-3000 mcg, Vitamin B6 0.1 mg-1000 mg. Vitamin D3 10 IU-10000 IU, Folic acid 10-5,000 mcg, L-proline 1 mg-20,000 mg, L-lysine 1 mcg-20000 mg, Copper 0.1 mg-15 mg. Betaine HCl 10 mg-2000 mg. Chondroitin sulfate 10 mg-10000 mg, N-acctyl-glucosamine 10 mg-50000 mg, Pycnogenol 5 mg-2,000 mg. SAMe 10 mg-10000 mg, Cat's claw 1 mg-10000 mg, Boswellia seirata 1 mg-10000 mg, Stinging nettle 1 mg-20000 mg and Glutamine 1 mg-10000 mg.

In one embodiment, the mammal is treated with the micronutrient composition to reduce pro-inflammatory IL-6 and decreased secretion of MMP13, the ECM damaging enzyme in joints. As an example one of the diseases is osteoarthritis. The micronutrient composition comprises of Vitamin C, Vitamin E (D-alpha tocopherol), Vitamin B6. Vitamin D3, Folic acid, L-proline, L-lysine, Copper, Betaine HCL, Chondroitin sulfate, N-acetyl-glucosamine. Pycnogenol, SAMe, Cat's claw. Boswellia serrata, Stinging nettle and Glutamine and specifically in the range of Vitamin C 10 mg-50000 mg, Vitamin E (D-alpha tocopherol) 1 mcg-3000 mcg, Vitamin B6 0.1 mg-1000 mg. Vitamin D3 10 IU-10000 IU, Folic acid 10-5,000 mcg, L-proline 1 mg-20,000 mg, L-lysine 1 mcg-20000 mg. Copper 0.1 mg-15 mg, Betaine HCl 10 mg-2000 mg. Chondroitin sulfate 10 mg-10000 mg, N-acetyl-glucosamine 10 mg-50000 mg, Pycnogenol 5 mg-2,000 mg. SAMe 10 mg-10000 mg, Cat's claw 1 mg-10000 mg, Boswellia serrata 1 mg-10000 mg, Stinging nettle 1 mg-20000 mg and Glutamine 1 mg-10000 mg. The micronutrient composition stated in the entire disclosure refers to Mix A. Finally, the present invention is described further in the detailed description to further illustrate various aspects of the present invention.

BRIEF DESCRIPTION OF DRAWINGS

Example embodiments are illustrated by way of example only and not limitation, with reference to the figures of the accompanying drawings, in which like references indicate similar elements and in which.

Figure 1:
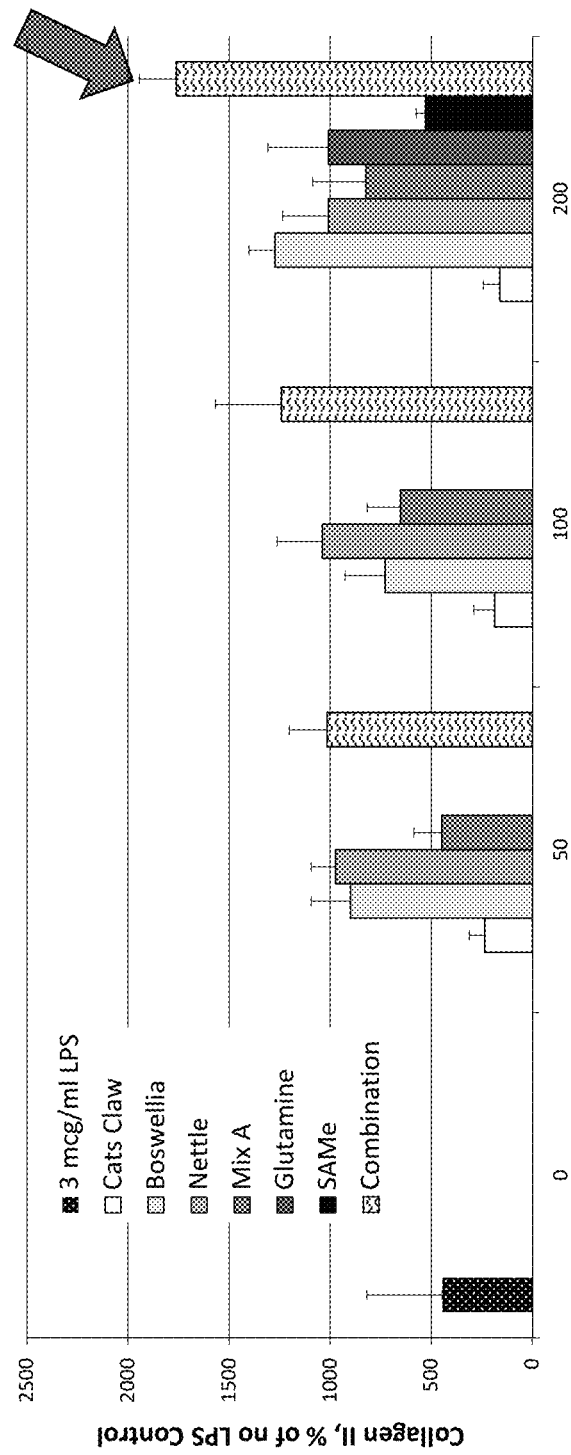
FIG. 1 shows effects of micronutrient composition on Collagen Type II Accumulation in Cultured Human Chondrocytes (HC).

Other features of the present disclosure will be apparent from the accompanying drawings and from the detailed description of embodiments that follows.

DETAILED DESCRIPTION

Many combinations of micronutrients have been used for treating and reducing high chronic arthritis in mammal. However, in the instant invention a combination of micronutrient composition makes a good combination shows unexpected results and effectiveness. The said range shown in the table is optimal for 1 dosage. However, the range for concentration may be broader or narrower than described. The combination of micronutrients may be taken as 1 dose or multiple doses. Chronic arthritis is a common disease affecting physical abilities and quality of life for millions of people around the word. Arthritis usually accompanies aging and also develops as a result of accumulated trauma and injury events.

Pathological changes in affected joints are characterized by dramatic change in the composition of synovial cartilage and fluid. Pathological process of arthritis development involves chronic inflammation which is aggravating arthritic manifestations.

The goal of this study was to investigate effects of some naturally occurring compounds that are formulated as suitable mode of administering to mammal suffering from the arthritic process using the experimental model of cultured human chondrocytes and synovial fibroblasts. Chronic arthritis is a commonly occurring disease affecting physical abilities and quality of life of millions of people around the word. Arthritis usually develops along with aging and also due to accumulated trauma and injury events.

Pathological changes in affected joints are characterized by dramatic alterations in the composition of synovial cartilage and fluid. Pathological process of arthritis development involves chronic inflammation which is aggravating arthritic manifestations.

Inflammation process was initiated by additions of bacterial lipopolysaccharide (LPS) to cell culture medium. Tested parameters included cellular release of interleukin 6 (IL6) as an indicator of induced inflammation, cell culture accumulation of specific extracellular matrix (ECM) components, such as collagen type II (Col2), aggrecan (Aggr) and hyaluronic acid (HA), and release of matrix metalloproteinase 13 (MMP13) as an indicator of cartilage digesting process. Addition of LPS to cell cultures induced inflammation process characterized by dramatic increase in cellular release of IL6 and MMP13 and reduction in cell culture content of Col2, Aggr and HA.

These arthritic processes were reversed to different degrees by cell culture medium additions of Cats Claw extract, Boswellia *Serrata* extract, Nettle Leaf extract, nutritional mixture Mix A, L-Glutamine, S-Adenosyl Methionine, Alpha Keto-Glutarate and Iron (II) Fumarate. Combination of all tested compounds had anti-arthritic effects superior to the use of individual components in all aspects tested in the study indicating its pleiotropic effect.

We conclude that naturally occurring compounds can diminish arthritic processes in cultured human synovial cells. These findings support an application of tested compound in prevention and treatment of human chronic arthritis.

Table 1: Shows the ingredients in various Micronutrient combinations and their concentration range:

| Individual Ingredients | Mix A | Mix B |
| --- | --- | --- |
| Vitamin C | 10 mg-50,000 mg | 10 mg-50,000 mg |
| Vitamin E (D-alpha tocopherol) | 1 mcg-3,000 mcg | 1 mcg-3,000 mcg |
| Vitamin B6 | 0.1 mg-1,000 mg | 0.1 mg-1,000 mg |
| Vitamin D3 | 10 IU-10,000 IU | 10 IU-10,000 IU |
| Folic acid | 10 mcg-5,000 mcg | 10 mcg-5,000 mcg |
| L-proline | 1 mg-20,000 mg | 1 mg-20,000 mg |
| L-lysine | 1 mg-20,000 mg | 1 mg-20,000 mg |
| Copper | 0.1 mg-15 mg | 0.1 mg-15 mg |
| Betaine HCl | 10 mg-2,000 mg | 10 mg-2,000 mg |
| Chondroitin sulfate | 10 mg-10,000 mg | 10 mg-10,000 mg |
| N-acetyl-glucosamine | 10 mg-50,000 mg | 10 mg-50,000 mg |
| Pycnogenol | 5 mg-2,000 mg | 5 mg-2,000 mg |
| SAMe | N/A | 10 mg-10,000 mg |
| Cat's claw | N/A | 1 mg-10,000 mg |
| Boswellia serrata | N/A | 1 mg-10,000 mg |
| Stinging nettle | N/A | 1 mg-20,000 mg |
| Glutamine | N/A | 1 mg-10,000 mg |

Physiological dose range for mammal consumption, such as human, has been calculated as follows: Vitamin C 10 mg-50000 mg. Vitamin E (D-alpha tocopherol) 1 mcg-3000 mcg, Vitamin B6 0.1 mg-1000 mg, Vitamin D3 10 IU-10000 IU, Folic acid 10-5,000 mcg, L-proline 1 mg-20,000 mg, L-lysine 1 mcg-20000 mg. Copper 0.1 mg-15 mg, Betaine H-Ci 10 mg-2000 mg, Chondroitin sulfate 10 mg-10000 mg. N-acclyl-glucosamine 10 mg-50000 mg. Pycnogenol 5 mg-2,000 mg. SAMe 10 mg-10000 mg, Cat's claw 1 mg-10000 mg, Boswellia serrata 1 mg-10000 mg, Stinging nettle 1 mg-20000 mg and Glutamine 1 mg-10000 mg. The physiological dose is shown in a range after calculating from in vivo studies, that it is suitable for various methods of delivery or consumption. Since different modes of delivery of micronutrient composition depend on many factors such as different absorption, severity, individual differences, absorption, but not limited to these.

Method of treating a mammal, such as human, to treat chronic arthritis joint inflammation using the micronutrient composition comprising in a range Vitamin C 10 mg-50000 mg, Vitamin E (D-alpha tocopherol) 1 mcg-3000 mcg. Vitamin B6 0.1 mg-1000 mg, Vitamin D3 10 IU-10000 IU, Folic acid 10-5,000 mcg, L-proline 1 mg-20,000 mg. L-lysine 1 mcg-20000 mg, Copper 0.1 mg-15 mg, Betaine HCl 10 mg-2000 mg. Chondroitin sulfate 10 mg-10000 mg. N-acetyl-glucosamine 10 mg-50000 mg. Pycnogenol 5 mg-2,000 mg, SAMe 10 mg-10000 mg, Cat's claw 1 mg-10000 mg, Boswellia serrata 1 mg-10000 mg, Stinging nettle 1 mg-20000 mg and Glutamine 1 mg-10000 mg. The described micronutrient composition may be used individually or in combination.

Materials and Methods: All reagents were purchased from Sigma-Aldrich except to other indications. Cats Claw and Boswellia *Serrata* extracts were supplied by Bulk Supplements. Nettle Leaf power was from Monterey Bay Spice Company. Arteriforte was supplied by Dr Rath Health program, BV. Bacterial lipopolysaccharide (LPS) was from Sigma-Aldrich. Stock solutions of above supplements were prepared in dimethyl sulfoxide (DMSO) at 100 mg/ml (LPS at 25 mg/ml). Stock solutions for L-Glutamine, S-Adenosyl Methionine (SAMe), Alpha Keto-Glutarate (AKG) and Iron (II) Fumarate (Fe) (all from Sigma-Aldrich) were prepared in deionized water at 10 mg/ml (Fe at 1 mg/ml). All stock solutions were aliquoted and stored at −20° C. before use. Final DMSO concentration in cell culture medium did not exceed 0.5%.

All compounds were tested individually, and as Mix 1 and Mix 2. The Composition was made by combining 40 mcl of each: Cats Claw Extract, Boswalia extract, Nettle Leaf extract and Mix 1 (100 mg/ml DMSO) with SAMe, Glutamine and AKG (10 mg/ml H20) and Fe (1 mg/ml H2O). The Combination stock solution concentration was considered as 100 mg/ml and used in experiments accordingly.

Cell culture experiments for effects of Micronutrient composition on production of Synovial Cartilage Components in Cultured Human Synovial Cells were done.

Cell culture: Human Synovial Firbroblasts (HSF), supplied by ScienCell) were subcultured in Synovicyte Medium (ScienCell) supplemented with 2% fetal bovine serum (FBS) and Synovicyte Growth Supplements (ScienCell) at 37° C. in 5% CO2 atmosphere. Human Chondrocytes (HC), supplied by Sigma-Aldrich) were subcultured in Chondrocyte Growth Medium supplemented with Chondrocyte Growth Medium Supplement Mix (Sigma-Aldrich) at 37° C. in 5% CO2 atmosphere. Cell culture medium was refreshed every 2-3 days.

Experiments: For the experiments cells were seeded in 96 well plastic cell culture plates covered with fibronectin (Greiner Bio-One) and grown to a confluent layer at 37° C. and 5% CO2 in corresponding cell culture medium. Cells were supplemented with 3 mcg/ml bacterial lipopolysaccharide (LPS, inflammation inducing treatment) and micronutrient composition were applied for indicated period in growth medium as indicated in the corresponding figure legends. At the end of the incubation cultured cells layers were washed twice with phosphate buffered saline (PBS) and treated in two ways: for the exposition of extracellular matrix (ECM) cells were lysed by 3 min incubation with 0.5% Triton X100/PBS which was followed by 3 min incubation with 25 mM NH4OH/PBS at room temperature or the cells were fixed by using 3% formaldehyde/PBS for one hour at 4° C. Treated cell layers were washed four times with PBS followed by one hour incubation with 1% bovine serum albumin (BSA) in PBS at RT.

Aggrecan, Collagen type II and Hyaluronic Acid content in 96 well plates prepared as described above, which is either exposed ECM or in fixed cells, was assayed by standard sandwich type immunoassay (ELISA, all reagents from Sigma-Aldrich) using rabbit polyclonal anti aggrecan, rabbit polyclonal anti collagen type II antibodies or biotinylated Hyaluronic Acid binding protein as primary treatment and goat anti rabbit IgG antibodies conjugated with horse radish peroxidase (HRP) or HRP-conjugated High Density Streptavidin as secondary treatment, respectively. Assayed component content was estimated by color changing reaction of HRP substrate (TMB substrate solution, Sigma-Aldrich) measured as 450 nm optical density using microplate optical density reader (Molecular Devices). Experiments were run at least in triplicates and results were presented as percentage of unsupplemented control (mean+/−SD).

Effects of Micronutrient composition on Release of Inflammation Markers in Cultured Human Synovial Cells: Inflammation process was induced in human chondrocytes cultured in 96 well plates with LPS as described above. Cells were supplemented with LPS and micronutrient composition as indicated in corresponding figure legends. At the end of indicated incubation period interleukin 6 (IL6) and matrix metalloproteinase 13 (MMP13) levels in conditioned cell culture media were measured by ELISA using assay kits (R&D Systems) in accordance with manufacturer's protocol. Experiments were run at least in triplicates and results were presented as percentage of unsupplemented control (mean+/−SD).

Figures present results from representative experiments out of at least three independent experiments with similar design. FIG. 1 shows effects of micronutrient composition on collagen type II accumulation in cultured human chondrocytes (HC). HC were seeded in fibronectin covered 96 well plates at 5th passage and grown in chondrocyte growth medium. Confluent HC cultures were supplemented with 3 mcg/ml LPS and tested compounds as indicated for 14 days. After incubation the cell produced extracellular matrix (ECM) was exposed by sequential treatment with 0.5% Triton X100 and 25 mM $NH_4OH$ in PBS. Collagen type II content in HC-produced ECM was determined by immunoassay. Results are presented as percentage of unsupplemented controls (average+/−SD, n=4). Combination of all ingredients as micronutrient composition as Mix 2 at 100 mcg/ml and 200 mcg/ml concentrations was most effective compared to individual ingredients and Mix 1. The Combination at 200 mcg/ml resulted in over 1700% increase in extracellular collagen II deposition compared to control. Combination of all ingredients Mix 2 at 100 mcg/ml and 200 mcg/ml concentrations was most effective compared to individual ingredients and Mix 1. The micronutrient composition comprising of said ingredients at 200 mcg/ml resulted in over 1700% increase in extracellular collagen II deposition compared to control. These are convincingly unprecedented results.

Figure 2:
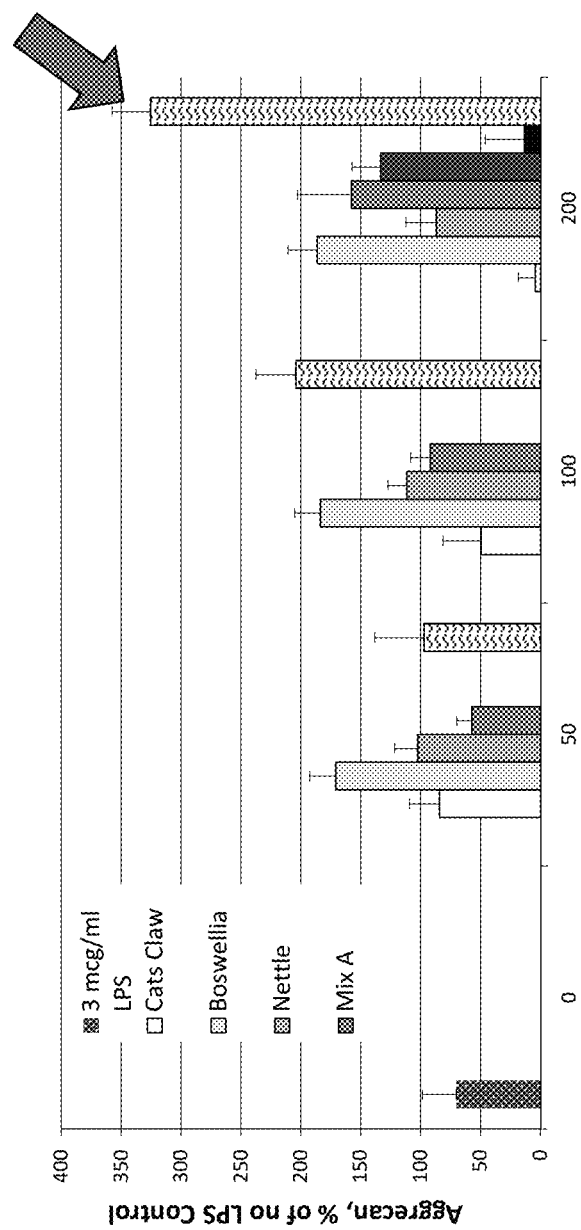
FIG. 2 shows effects of micronutrient composition on Aggrecan Accumulation in ECM produced by Human Chondrocytes (HC).

FIG. 2 shows effects of micronutrient composition on Aggrecan Accumulation in Cultured Human Chondrocytes (HC). HC were seeded in fibronectin covered 96 well plates at 5th passage and grown in Chondrocyte Growth Medium. Confluent HC cultures were supplemented with 3 mcg/ml LPS and micronutrient composition as indicated in the graphs and incubated for 14 days. After the incubation cell produced extracellular matrix (ECM) was exposed by sequential treatment with 0.5% Triton X100 and 25 mM NH4OH in PBS. Aggrecan content in HC-produced ECM was assayed by immunoassay. Results are presented as percentage of unsupplemented controls (average+/−SD, n=4). Micronutrient composition Mix 1 as a combination of all ingredients at concentration of 200 mcg/ml was significantly more effective compared to other test ingredients and it resulted in over 320% increase in extracellular aggrecan deposition compared to control.

Figure 3:
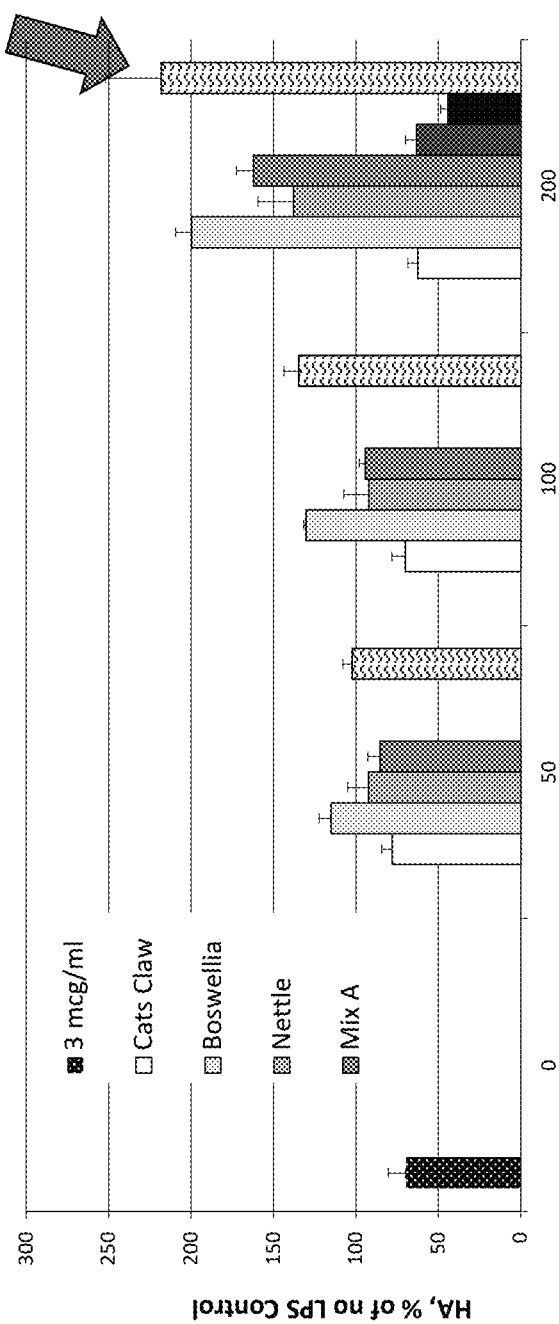
FIG. 3 shows effects of micronutrient composition on Hyaluronic Acid Synthesis in Cultured Human Chondrocytes (HC).

FIG. 3 shows effects of micronutrient composition on Hyaluronic Acid Accumulation in Cultured Human Chondrocytes (HC). HC were seeded in fibronectin covered 96 well plates at 5th passage and grown in Chondrocyte Growth Medium. Confluent HC cultures were supplemented with 3 mcg/ml LPS and micronutrient composition as indicated in the graph for 14 days. After the incubation cell layers were fixed with 3% formaldehyde/PBS and HC HA content was determined as described in Materials and Methods. Results are presented as percentage of unsupplemented controls (average+/−SD, n=4). Combination of all ingredients as a micronutrient composition at concentration of 200 mcg/ml resulted in over 200% increase in hyaluronic acid synthesis in chondrocytes compared to control. This is not only unexpected but also shows the effectiveness of the micronutrient composition.

Figure 4A:
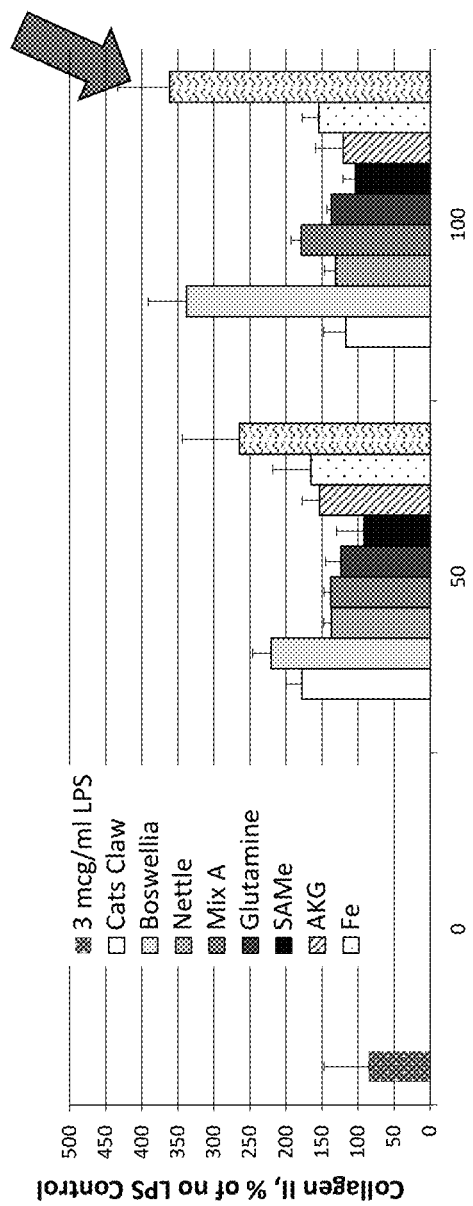
FIG. 4A shows effects of micronutrient composition on Collagen type II Accumulation in Cultured Human Synovial Fibroblasts (HSF).
Figure 4B:
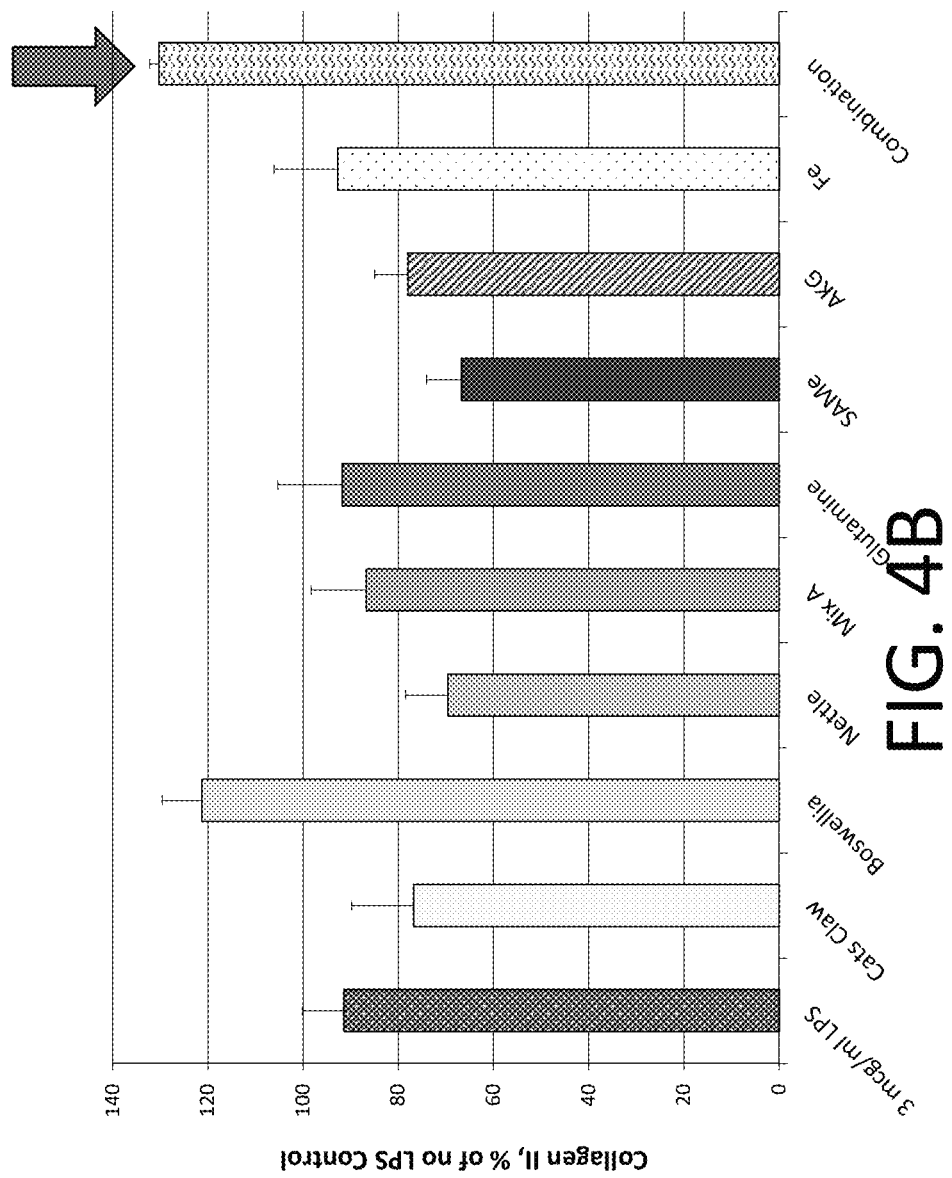
FIG. 4B shows effects of micronutrient composition on Collagen type II Accumulation in Cultured Human Synovial Fibroblasts (HSF).

FIG. 4A and FIG. 4B shows effects of Micronutrient composition on Collagen type II accumulation in Cultured Human Synovial Fibroblasts (HSF). HSF were seeded in fibronectin covered 96 well plates at 5th passage and grown in Synovicyte Growth Medium. Confluent HSF cultures were supplemented with 3 mcg/ml LPS and micronutrient composition as indicated in the graph and incubated for 7 days. After the incubation cell layers were either fixed with 3% formaldehyde in PBS (FIG. 4B) or cell produced extracellular matrix (ECM) (FIG. 4A) was exposed by sequential treatment with 0.5% Triton X100 and 25 mM NH4OH in PBS. Collagen type II content in HSF (B) and HSF-produced ECM (A) was assayed by immunoassay. Results are presented as percentage of unsupplemented controls (average+/−SD, n=4). Unprecedented result were shown with combination of all ingredients was more effective than individual compounds and Mix A at both tested concentrations. At concentration of 100 mcg/ml increased collagen deposition in ECM by synovial fibroblasts by 338% compared to unsupplemented control. FIG. 4B shows 130% increase in collagen II production in the synovial fibroblast cells in presence of combination of all ingredients at 50 mcg/ml.

Figure 5A:
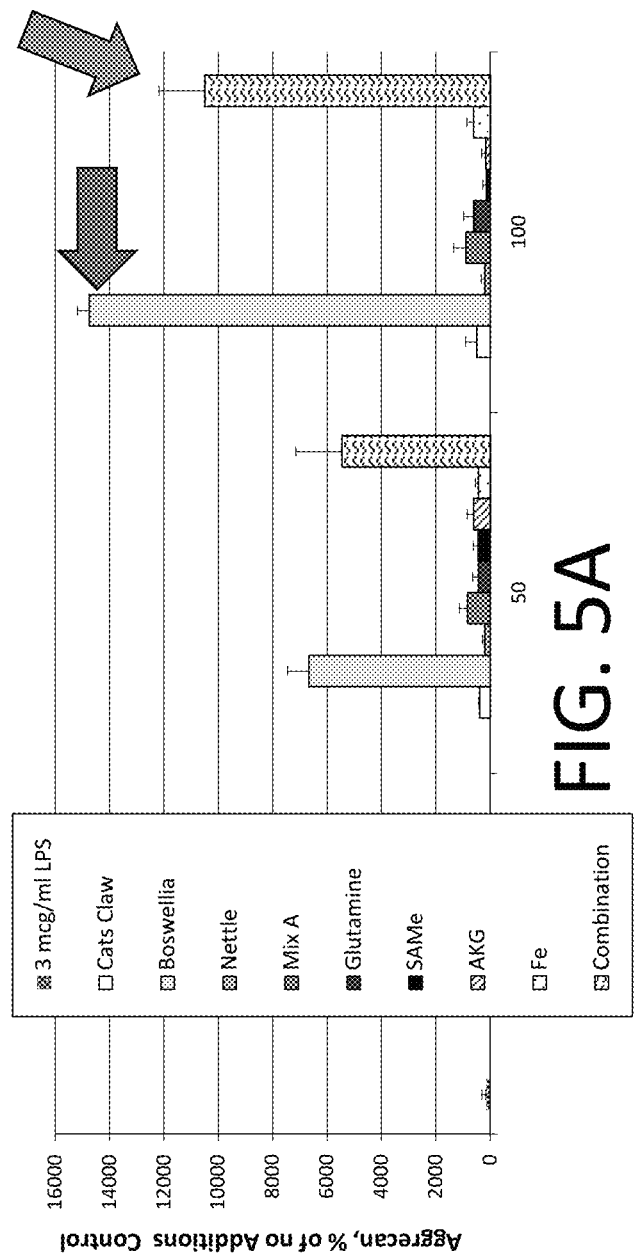
FIG. 5A shows effects of micronutrient composition on Aggrecan accumulation in Cultured Human Synovial Fibroblasts (HSF).
Figure 5B:
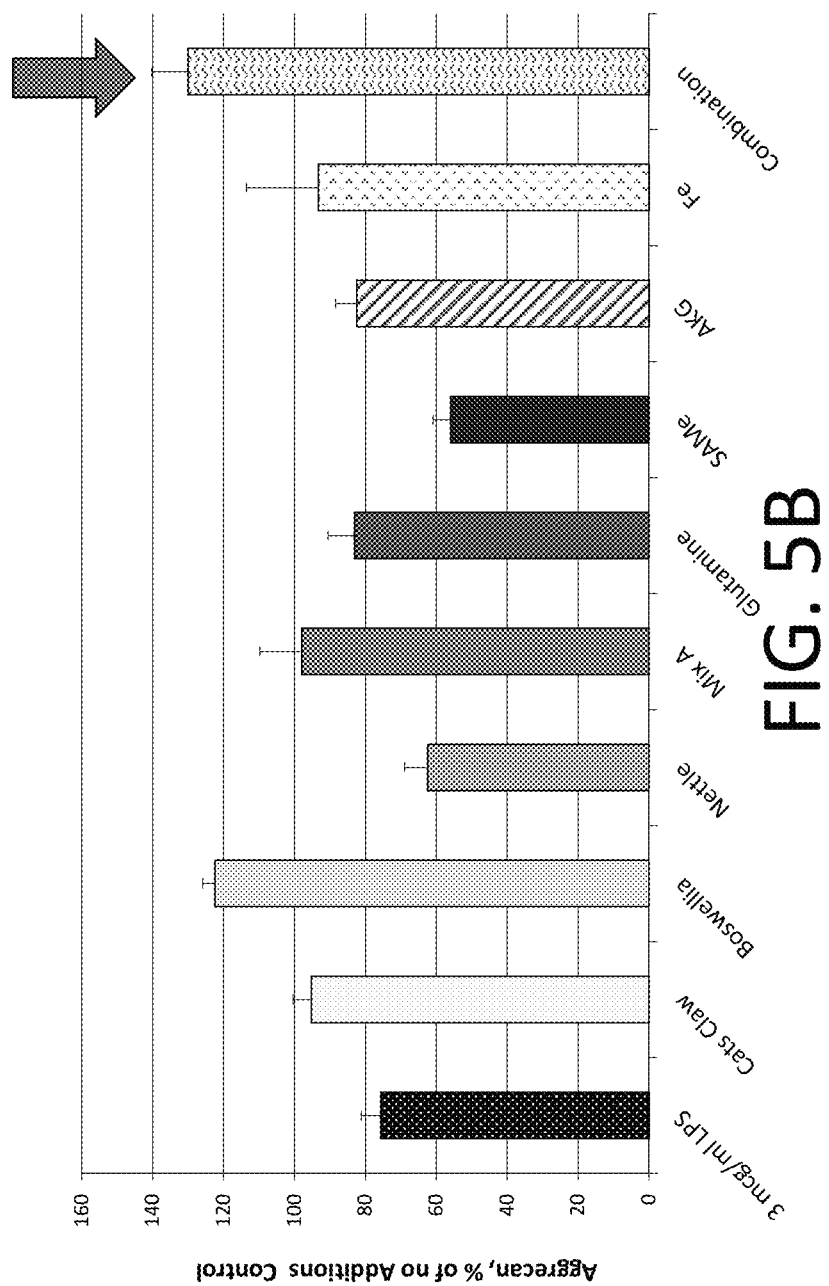
FIG. 5B shows effects of micronutrient composition on Aggrecan accumulation in Cultured Human Synovial Fibroblasts (HSF).

FIG. 5A and FIG. 5B shows effects of micronutrient composition individually and as a micronutrient composition on Aggrecan accumulation in Cultured Human Synovial Fibroblasts (HSF). HSF were seeded in fibronectin covered 96 well plates at 5th passage and grown in Synovicyte Growth Medium. Confluent HSF cultures were supplemented with 3 mcg/ml LPS and micronutrient composition as indicated in the graph and incubated for 7 days. After the incubation cell layers were either fixed with 3% formaldehyde in PBS (FIG. 5B) or cell produced extracellular matrix (ECM) (FIG. 5A) was exposed by sequential treatment with 0.5% Triton X100 and 25 mM NH4OH in PBS. Aggrecan content in HSF (B) and HSF-produced ECM (A) was assayed by immunoassay. Results are presented as percentage of unsupplemented controls (average+/−SD, n=4). Micronutrient composition in FIG. 5A shows that at 100 mcg/ml resulted in over 10500% increase in aggrecan extracellular deposition. Boswellia applied individually at the same concentration was more effective than the combination on aggrecan deposition in ECM (over 14700% increase).

However, it appears that the micronutrient composition has more diverse beneficial effects compared to Boswellia (based on its efficacy on other ECM components and anti-inflammatory effects seen in other data). FIG. 5B shows maximum aggrecan production (130% increase) in synovial fibroblasts was observed the presence of the micronutrient composition at 50 mcg/ml.

Figure 6A:
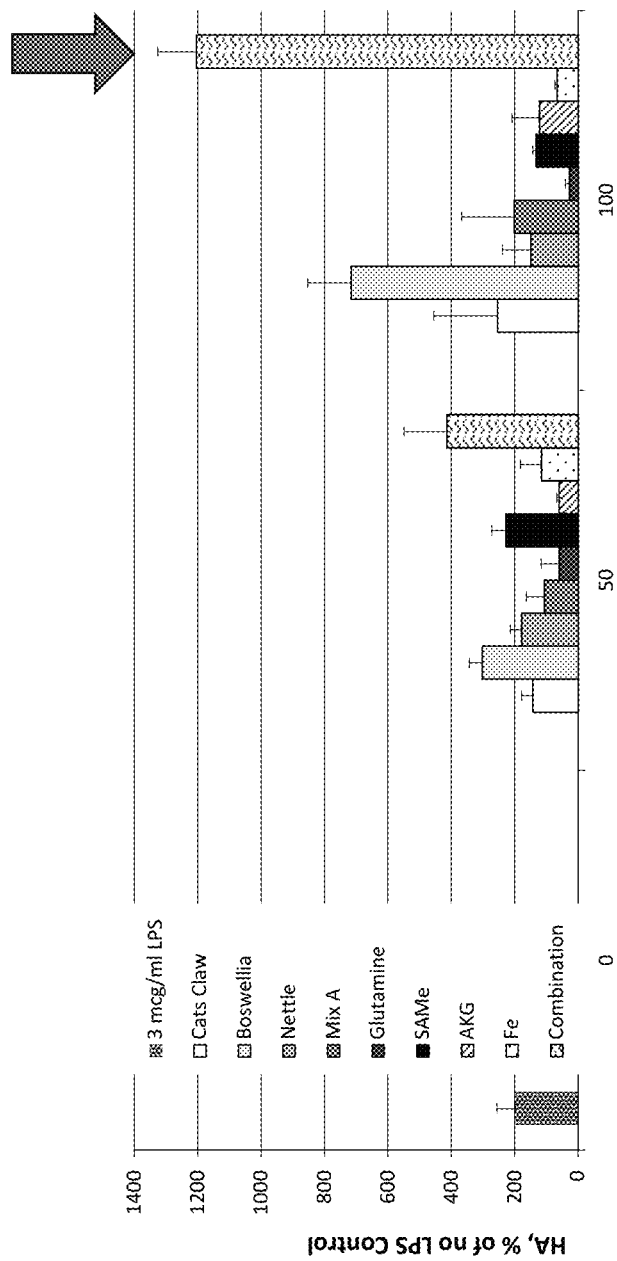
FIG. 6A shows effects of micronutrient composition on Hyaluronic Acid accumulation in Cultured Human Synovial Fibroblasts (HSF).
Figure 6B:
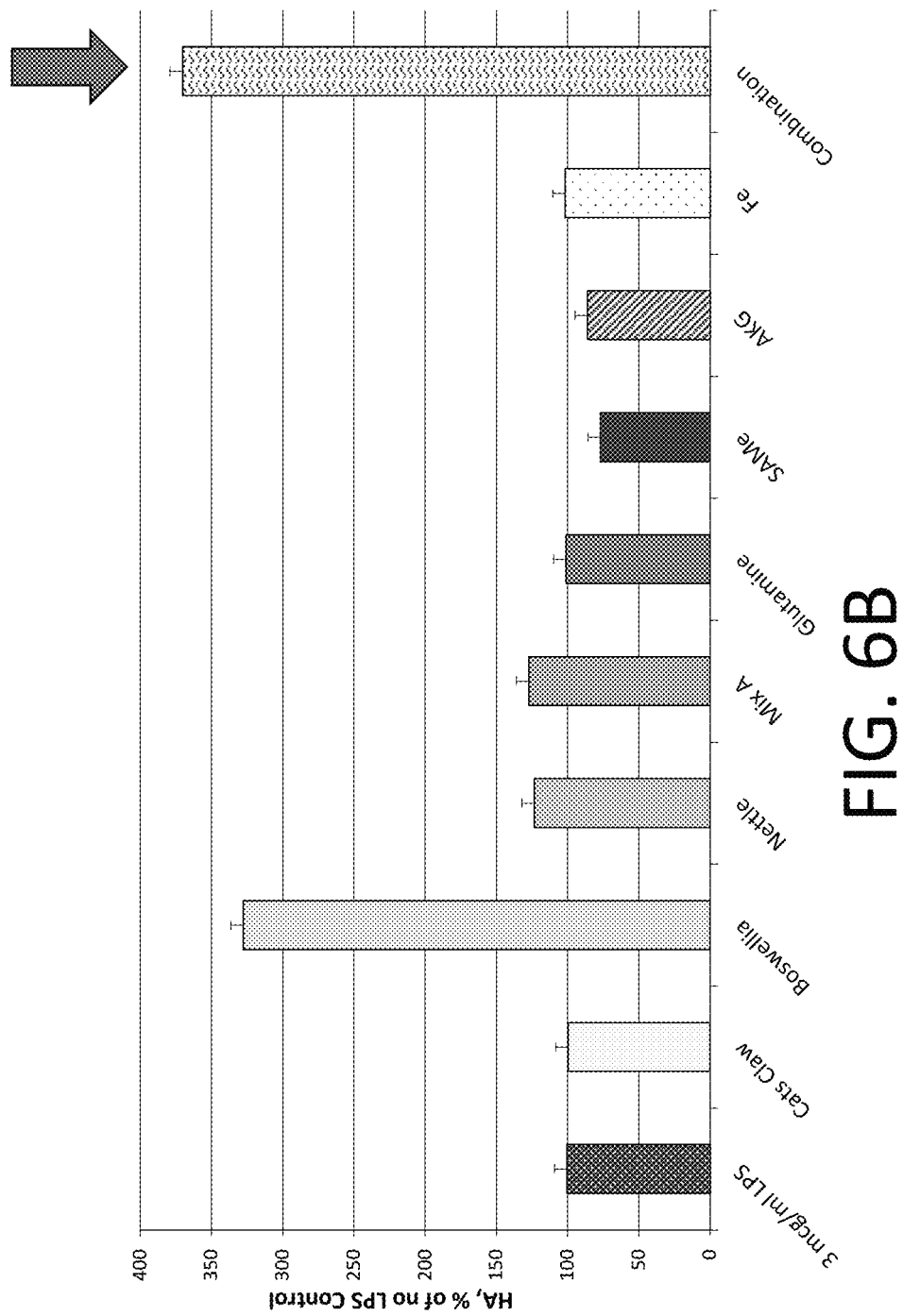
FIG. 6B shows effects of micronutrient composition on Hyaluronic Acid accumulation in Cultured Human Synovial Fibroblasts (HSF).

FIGS. 6A and 6B shows effects of Micronutrient composition on Hyaluronic Acid accumulation in Cultured Human Synovial Fibroblasts (HSF). HSF were seeded in fibronectin covered 96 well plates at 5th passage and grown in Synovicyte Growth Medium. Confluent HSF cultures were supplemented with 3 mcg/ml LPS and micronutrient composition as indicated in the graph and incubated for 7 days. After the incubation cell layers were either fixed with 3% formaldehyde in PBS (FIG. 6B) or cell produced extracellular matrix (ECM) (FIG. 6A) was exposed by sequential treatment with 0.5% Triton X100 and 25 mM NH4OH in PBS. Hyaluronic Acid content in HSF (FIG. 6B) and HSF-produced ECM (FIG. 6 A) was determined using biotinylated HA-binding protein and HRP-Streptavidin conjugate as described in Materials and Methods. Results are presented as percentage of unsupplemented controls (average+/−SD, n=4). FIG. 6A showed micronutrient composition at concentrations of 50 and 100 mcg/ml was the most effective. At 200 mcg/ml it resulted in over 1200% increase in extracellular deposition of hyaluronic acid, FIG. 6B showed maximum hyaluronic acid accumulation (over 370% increase) in synovial fibroblasts was observed the presence of the micronutrient composition at 50 mcg/ml.

Figure 7:
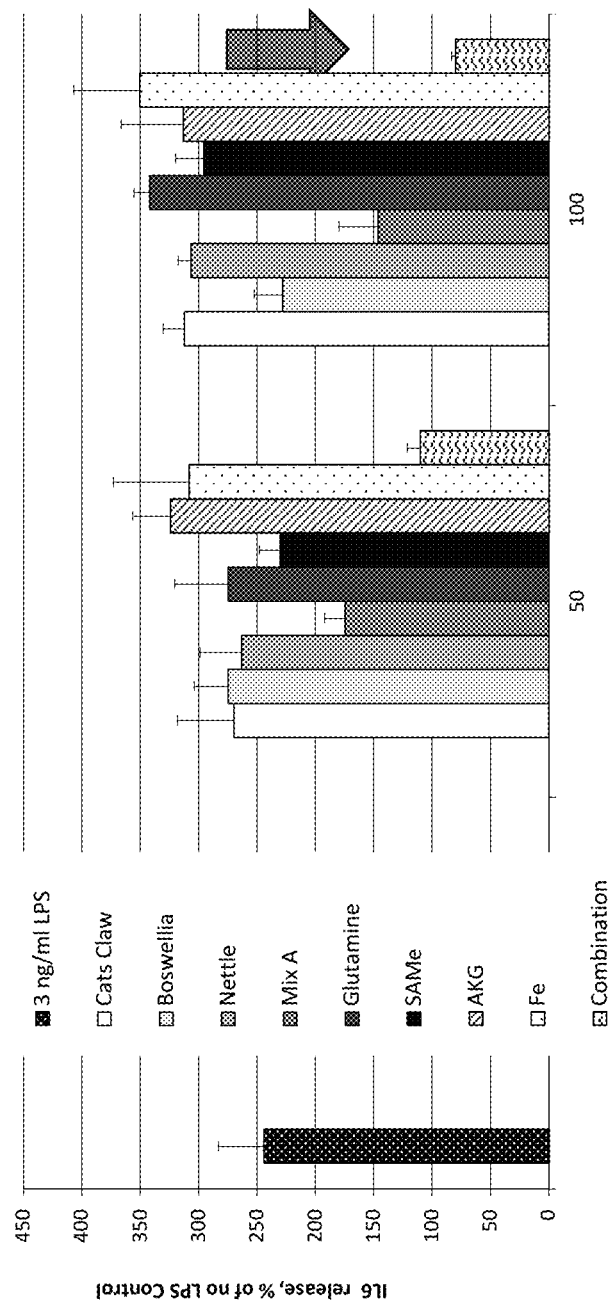
FIG. 7 shows effects of micronutrient composition on Interleukin 6 (IL6) secretion in Cultured Human Chondrocytes (HC).

FIG. 7 shows effects of Micronutrient composition on Interleukin 6 (IL6) production in Cultured Human Chondrocytes (HC). HC were seeded in fibronectin covered 96 well plates at 5th passage and grown in Chondrocyte Growth Medium. Confluent HC cultures were supplemented with 3 ng/ml LPS and micronutrient composition as indicated on the graph for 2 hours. After incubation IL6 content in cell culture conditioned media was assayed by ELISA as described in Materials and methods. Results are presented as percentage to unsupplemented controls (average+/−SD, n=4). FIG. 7 shows maximum decrease in IL-6 secretion was observed in the presence of the combination of all ingredients at 50 and 100 mcg/ml compared to other micronutrient composition. IL6 secretion in chondrocytes decreased from 244% in the presence of LPS to 80% in the presence of LPS plus the micronutrient composition.

Figure 8:
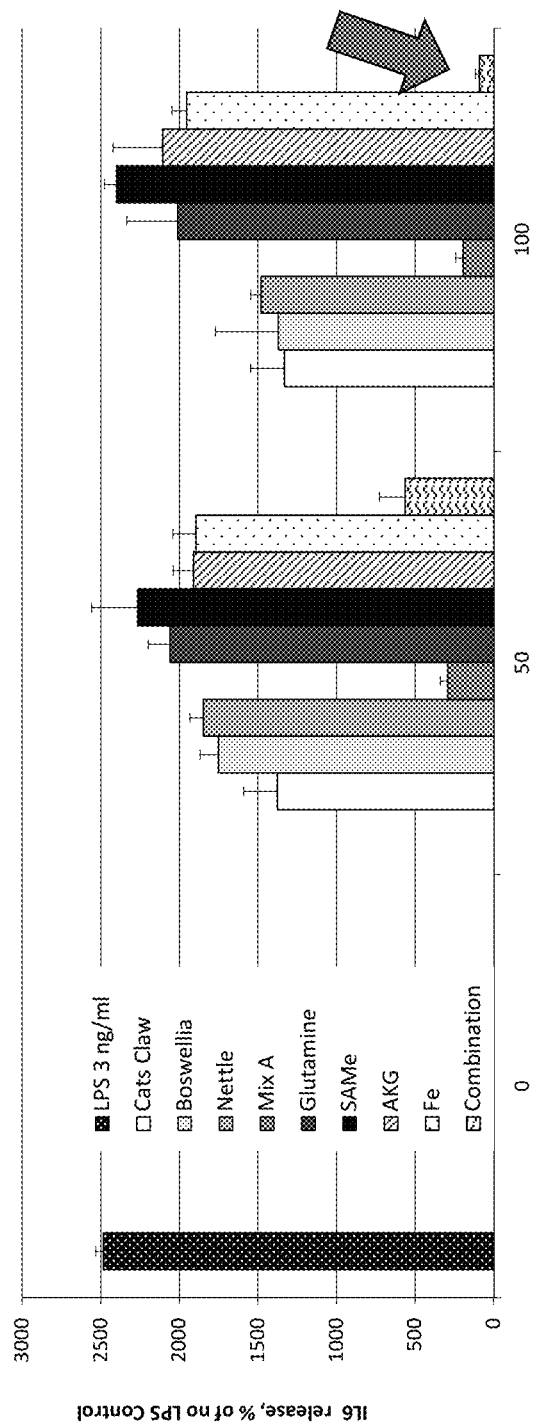
FIG. 8 shows effects of micronutrient composition on Matrix Metalloproteinase 13 (MMP13) secretion in Cultured Human Chondrocytes (HC).

FIG. 8 shows effects of micronutrient composition on Matrix Metalloproteinase 13 (MMP13) secretion by Cultured Human Chondrocytes (HC). HC were seeded in fibronectin covered 96 well plates at 5th passage and grown in Chondrocyte Growth Medium. Confluent HC cultures were supplemented with 3 ng/ml LPS and micronutrient composition as indicated in the graph and incubated for 2 hours. Subsequently, MMP13 content in cell culture conditioned media was assayed by ELISA as described in Materials and Methods. Results are presented as percentage of unsupplemented controls (average+/−SD, n=4). FIG. 8 shows Maximum decrease in MMP13 secretion (enzyme destroying ECM) in chondrocytes by micronutrient composition at 100 mcg/ml. A decrease from 2484% in LPS Control to 93% in the presence of LPS plus the micronutrient composition. In conclusion the final micronutrient composition (referred to as combination in the instant specification) is composed of Mix A with other micronutrients. The micronutrient composition comprised of Vitamin C, Vitamin E (D-alpha tocopherol), Vitamin B6. Vitamin D3, Folic acid, L-proline, L-lysine, Copper, Betaine HCl, Chondroitin sulfate, N-acetyl-glucosamine. Pycnogenol, SAMe. Cat's claw. Boswellia serrata. Stinging nettle and Glutamine. The respective components of the micronutrient mixture (shown in figures as combination) are in the range of Vitamin C 10 mg-50,000 mg. Vitamin E (D-alpha tocopherol) 1-3,000 mcg, Vitamin B6 0.1-1,000 mg. Vitamin D3 10 IU-10,000 IU, Folic acid 10-5,000 mcg. L-proline 1-20,000 mg. L-lysine 1-20,000 mg, Copper 0.1-15 mg, Betaine HCl 10-2,000 mg, Chondroitin sulfate 10-10,000 mg, N-acetyl-glucosamine 10-50,000 mg, Pycnogenol 5-2,000 mg, SAMe 10-10,000 mg, Cat's claw 1-10,000 mg, Boswellia serrata 1-10,000 mg, Stinging nettle 1-20,000 mg and Glutamine 1-10,000 mg. In another embodiment, the micronutrient composition consist of Vitamin C, Vitamin E (D-alpha tocopherol), Vitamin B6, Vitamin D3. Folic acid. L-proline, L-lysine, Copper. Betaine HCl, Chondroitin sulfate. N-acetyl-glucosamine, Pycnogenol, SAMe, Cat's claw, Boswellia serrata, Stinging nettle and Glutamine. The respective components of the micronutrient mixture (shown in figures as combination) are in the range of Vitamin C 10 mg-50,000 mg, Vitamin E (D-alpha tocopherol) 1-3,000 mcg, Vitamin B6 0.1-1,000 mg, Vitamin D3 10 IU-10,000 IU, Folic acid 10-5,000 mcg, L-proline 1-20,000 mg, L-lysine 1-20,000 mg. Copper 0.1-15 mg, Betaine HCl 10-2,000 mg, Chondroitin sulfate 10-10,000 mg, N-acetyl-glucosamine 10-50,000 mg, Pycnogenol 5-2,000 mg, SAMe 10-10,000 mg, Cat's claw 1-10,000 mg, Boswellia serrata 1-10,000 mg, Stinging nettle 1-20,000 mg and Glutamine 1-10,000 mg. It demonstrated the highest efficacy compared to other ingredients in simultaneously supporting critical cellular mechanisms important for healthy joints.

The combination-increased production and extracellular deposition of key important ECM components (Collagen II, Aggrecan and Hyaluronic acid) by synovial cells and chondrocytes under pro-inflammatory conditions (presence of LPS):
  decreased pro-inflammatory IL-6
  decreased secretion of MMP13 (the ECM damaging enzyme in joints)

Several formulations are prepared to make said micronutrient composition to be administered to a mammal. Physiological doses are calculated and each dose is administered to reduce arthritic patients or any joint pain or patients suffering from joint illness pertaining to inflammation, joints damaged by enzymes, and increase deposition of key important ECM components to treat, prevent and repair the joints and the specific dose are given as one oral capsule once a day, twice a day or three times a day if the formulation is oral. Formulations suitable for oral administration may be in the form of capsules, cachets, pills, tablets, lozenges (using a flavored bases, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin or sucrose and acacia), each containing a predetermined amount of a subject composition as an active ingredient. Subject compositions may also be administered as a bolus, electuary or paste.

When an oral solid drug product is prepared, micronutrient composition is mixed with an excipient (and, if necessary, one or more additives such as a binder, a disintegrant, a lubricant, a coloring agent, a sweetening agent, and a flavoring agent), and the resultant mixture is processed through a routine method, to thereby produce an oral solid drug product such as tablets, coated tablets, granules, powder or capsules. Additives may be those generally employed in the art. Examples of excipients include lactate, sucrose, sodium chloride, glucose, starch, calcium carbonate, kaolin, microcrystalline cellulose and silicic acid. Binders include water, ethanol, propanol, simple syrup, glucose solution, starch solution, liquefied gelatin, carboxymethylcellulose, hydroxypropyl cellulose, hydroxypropyl starch, methyl cellulose, ethyl cellulose, shellac, calcium phosphate and polyvinyl pyrrolidone. Disintegrants include dried starch, rice powder, L-leucine, sodium arginate, powdered agar, sodium hydroxy carbonate, calcium carbonate, sodium lauryl sulfate, monoglyceryl stearate and lactose. Lubricants include purified talc, stearic acid salts, borax and polyethylene glycol. Sweetening agents include sucrose, orange peel, citric acid and tartaric acid.

When a liquid drug product for oral administration is prepared, micronutrient composition is mixed with an additive such as a sweetening agent, a buffer, a stabilizer, or a flavoring agent, and the resultant mixture is processed through a routine method, to produce an orally administered liquid drug product such as an internal solution medicine, syrup or elixir. Examples of the sweetening agent include vanillin; examples of the buffer include sodium citrate; and examples of the stabilizer include tragacanth, acacia, and gelatin.

For the purposes of transdermal (e.g., topical) administration, dilute sterile, aqueous or partially aqueous solutions (usually in about 0.1% to 5% concentration), otherwise similar to the above parenteral solutions, may be prepared with micronutrient composition.

Formulations containing micronutrient composition for rectal or vaginal administration may be presented as a suppository, which may be prepared by mixing a subject composition with one or more suitable non-irritating carriers, comprising, for example, cocoa butter, polyethylene glycol, a suppository wax or a salicylate, which is solid at room temperature, but liquid at body temperature and, therefore, will melt in the appropriate body cavity and release the encapsulated compound(s) and composition(s). Formulations that are suitable for vaginal administration also include pessaries, tampons, creams, gels, pastes, foams or spray formulations containing such carriers as are known in the art to be appropriate.

A targeted-release portion for capsules containing micronutrient composition can be added to the extended-release system by means of either applying an immediate-release layer on top of the extended release core; using coating or compression processes, or in a multiple-unit system such as a capsule containing extended- and immediate-release beads.

When used with respect to a micronutrient composition, the term "sustained release" is art recognized. For example, a therapeutic composition that releases a substance over time may exhibit sustained-release characteristics, in contrast to a bolus type administration in which the entire amount of the substance is made biologically available at one time. In particular embodiments, upon contact with body fluids, including blood, spinal fluid, mucus secretions, lymph or the like, one or more of the pharmaceutically acceptable excipients may undergo gradual or delayed degradation (e.g., through hydrolysis), with concomitant release of any material incorporated therein, e.g., a therapeutic and/or biologically active salt and/or composition, for a sustained or extended period (as compared with the release from a bolus). This release may result in prolonged delivery of therapeutically effective amounts of any of the therapeutic agents disclosed herein.

Current efforts in the area of drug delivery include the development of targeted delivery, in which the drug is only active in the target area of the body (for example, mucous membranes such as in the nasal cavity), and sustained-release formulations, in which the micronutrient composition is released over a period of time in a controlled manner from a formulation. Types of sustained release formulations include liposomes, drug-loaded biodegradable microspheres and micronutrient composition polymer conjugates.

Delayed-release dosage formulations are created by coating a solid dosage form with a film of a polymer, which is insoluble in the acid environment of the stomach, but soluble in the neutral environment of the small intestine. The delayed-release dosage units can be prepared, for example, by coating a micronutrient composition with a selected coating material. The micronutrient composition may be a tablet for incorporation into a capsule, a tablet for use as an inner core in a "coated core" dosage form, or a plurality of drug-containing beads, particles or granules, for incorporation into either a tablet or a capsule. Preferred coating materials include bioerodible, gradually hydrolysable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract, or slowly erode as the dosage form passes through the gastrointestinal tract, while enzymatically degradable polymers are degraded by bacterial enzymes present in the lower gastrointestinal tract, particularly in the colon. Alternatively, a delayed-release tablet may be formulated by dispersing a drug within a matrix of a suitable material such as a hydrophilic polymer or a fatty compound. Suitable hydrophilic polymers include, but are not limited to, polymers or copolymers of cellulose, cellulose ester, acrylic acid, methacrylic acid, methyl acrylate, ethyl acrylate and vinyl or enzymatically degradable polymers or copolymers as described above. These hydrophilic polymers are particularly useful for providing a delayed-release matrix. Fatty compounds for use as a matrix material include, but are not limited to, waxes (e.g., carnauba wax) and glycerol tristearate. Once the active ingredient is mixed with the matrix material, the mixture can be compressed into tablets.

A pulsed-release dosage is one that mimics a multiple dosing profile without repeated dosing, and typically allows at least a twofold reduction in dosing frequency as compared with the drug presented as a conventional dosage form (e.g., as a solution or prompt drug-releasing, conventional solid dosage form). A pulsed-release profile is characterized by a time period of no release (lag time) or reduced release, followed by rapid drug release. These can be formulated for critically ill patients using the instant micronutrient composition.

The phrases "parenteral administration" and "administered parenterally" as used herein refer to modes of administration other than enteral and topical, such as injections, and include without limitation intravenous, intramuscular, intrapleural, intravascular, intrapericardial, intra-arterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

Certain micronutrient composition disclosed herein, suitable for parenteral administration, comprise one or more subject compositions in combination with one or more pharmaceutically acceptable sterile, isotonic, aqueous, or non-aqueous solutions, dispersions, suspensions or emulsions, or sterile powders, which may be reconstituted into sterile injectable solutions or dispersions just prior to use, and which may contain antioxidants, buffers, bacteriostats, solutes that render the formulation isotonic within the blood of the intended recipient, or suspending or thickening agents.

When an injection product is prepared, micronutrient composition is mixed with an additive such as a pH regulator, a buffer, a stabilizer, an isotonicity agent or a local anesthetic, and the resultant mixture is processed through a routine method, to thereby produce an injection for subcutaneous injection, intramuscular injection, or intravenous injection. Examples of the pH regulator or buffer include sodium citrate, sodium acetate and sodium phosphate; examples of the stabilizer include sodium pyrosulfite, EDTA, thioglycolic acid, and thiolactic acid; examples of the local anesthetic include procaine hydrochloride and lidocaine hydrochloride; and examples of the isotonicity agent include sodium chloride and glucose.

The phrase "pharmaceutically acceptable" is art recognized. In certain embodiments, the term includes compositions, polymers and other materials and/or dosage forms that are within the scope of sound medical judgment, suitable for use in contact with the tissues of mammals, both human beings and animals, without excessive toxicity, irritation, allergic response or other problem or complication, commensurate with a reasonable benefit-risk ratio.

The phrase "pharmaceutically acceptable carrier" is art recognized, and includes, for example, pharmaceutically acceptable materials, compositions or vehicles, such as a liquid or solid filler, diluent, solvent or encapsulating material involved in carrying or transporting any subject composition from one organ or portion of the body, to another organ or portion of the body. Each carrier must be "acceptable" in the sense of being compatible with the other ingredients of a subject composition, and not injurious to the patient. In certain embodiments, a pharmaceutically acceptable carrier is non-pyrogenic. Some examples of materials that may serve as pharmaceutically acceptable carriers include: (1) sugars, such as lactose, glucose and sucrose; (2) starches, such as corn starch and potato starch; (3) cellulose and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, the micronutrient compositions described herein are formulated in a manner such that said compositions will be delivered to a mammal in a therapeutically effective amount, as part of a prophylactic, or therapeutic treatment to facilitate joint repair.

In certain embodiments, the dosage of the micronutrient compositions, which may be referred to as therapeutic composition provided herein, may be determined by reference to the plasma concentrations of the therapeutic composition or other encapsulated materials.

The therapeutic micronutrient composition provided by this application may be administered to a subject in need of treatment by a variety of conventional routes of administration, including orally, topically, parenterally, e.g., intravenously, subcutaneously or intramedullary. Further, the therapeutic compositions may be administered intranasally, as a rectal suppository, or using a "flash" formulation, i.e., allowing the medication to dissolve in the mouth without the need to use water. Furthermore, the compositions may be administered to a subject in need of treatment by controlled-release dosage forms, site-specific drug delivery, transdermal drug delivery, patch-mediated drug delivery (active/passive), by stereotactic injection, or in nanoparticles.

Expressed in terms of concentration, an active ingredient can be present in the therapeutic compositions of the present invention for localized use via the cutis, intranasally, pharyngolaryngeally, bronchially, intravaginally, rectally or ocularly.

For use as aerosols, the active ingredients can be packaged in a pressurized aerosol container together with a gaseous or liquefied propellant, for example dichlorodifluoromethane, carbon dioxide, nitrogen, propane and the like, with the usual adjuvants such as cosolvents and wetting agents, as may be necessary or desirable. The most common routes of administration also include the preferred transmucosal (nasal, buccal/sublingual, vaginal, ocular and rectal) and inhalation routes.

In addition, in certain embodiments, the subject micronutrient composition of the present application may be lyophilized or subjected to another appropriate drying technique such as spray drying. The subject compositions may be administered once, or may be divided into a number of smaller doses to be administered at varying intervals of time, depending in part on the release rate of the compositions and the desired dosage.

Formulations useful in the methods provided herein include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of a subject micronutrient composition that may be combined with a carrier material to produce a single dose may vary depending upon the subject being treated and the particular mode of administration.

The therapeutically acceptable amount described herein may be administered in inhalant or aerosol formulations. The inhalant or aerosol formulations may comprise one or more agents, such as adjuvants, diagnostic agents, imaging agents, or therapeutic agents useful in inhalation therapy. The final aerosol formulation may, for example, contain 0.005-90% w/w, for instance 0.005-50%, 0.005-5% w/w, or 0.01-1.0% w/w, of medicament relative to the total weight of the formulation.

Examples of suitable aqueous and non-aqueous carriers that may be employed in the micronutrient composition include water, ethanol, polyols (such as glycerol, propylene glycol, polyethylene glycol and the like), and suitable mixtures thereof, vegetable oils such as olive oil, and injectable organic esters such as ethyl oleate. Proper fluidity may be maintained, for example by the use of coating materials such as lecithin, by the maintenance of the required particle size in the case of dispersions, and by the use of surfactants.

INDUSTRIAL USE

Thus, in this study we prove that micronutrient composition plays a decisive role in regulating the joint mechanism by enhancing ECM related components in individuals. With optimum combination of natural ingredients and micronutrients formulated in various forms for a suitable consumption to prevent and treat arthritic patient is described.

What is claimed is:

1. A chronic arthritis reducing micronutrient composition, comprising:
   A Vitamin C 10 mg-50000 mg, Vitamin E (D-alpha tocopherol) 1 mcg-3000 mcg, Vitamin B6 0.1 mg-1000 mg, Vitamin D3 10 IU-10000 IU, Folic acid 10-5,000 mcg, L-proline 1 mg-20,000 mg, L-lysine 1 mcg-20000 mcg, Copper 0.1 mg-15 mg, Betaine HCl 10 mg-2000 mg, Chondroitin sulfate 10 mg-10000 mg, N-acetyl-glucosamine 10 mg-50000 mg, Pycnogenol 5 mg-2,000 mg, SAMe 10 mg-10000 mg, Cat's claw 1 mg-10000 mg, Boswellia serrata 1 mg-10000 mg, Stinging nettle 1 mg-20000 mg and Glutamine 1 mg-10000 mg formulated in a specific form for mammal consumption.

2. The micronutrient composition of claim 1, consisting of the Vitamin C 10 mg-50000 mg, Vitamin E (D-alpha tocopherol) 1 mcg-3000 mcg, Vitamin B6 0.1 mg-1000 mg, Vitamin D3 10 IU-10000 IU, Folic acid 10-5,000 mcg, L-proline 1 mg-20,000 mg, L-lysine 1 mcg-20000 mg, Copper 0.1 mg-15 mg, Betaine HCl 10 mg-2000 mg, Chondroitin sulfate 10 mg-10000 mg, N-acetyl-glucosamine 10 mg-50000 mg, Pycnogenol 5 mg-2,000 mg, SAMe 10 mg-10000 mg, Cat's claw 1 mg-10000 mg, Boswellia serrata 1 mg-10000 mg, Stinging nettle 1 mg-20000 mg and Glutamine 1 mg-10000 mg.

3. The micronutrient composition, consisting of:
   A Vitamin C 10 mg-50000 mg, Vitamin E (D-alpha tocopherol) 1 mcg-3000 mcg, Vitamin B6 0.1 mg-1000 mg, Vitamin D3 10 IU-10000 IU, Folic acid 10-5,000 mcg, L-proline 1 mg-20,000 mg, L-lysine 1 mcg-20000 mg, Copper 0.1 mg-15 mg, Betaine HCl 10 mg-2000 mg, Chondroitin sulfate 10 mg-10000 mg, N-acetyl-glucosamine 10 mg-50000 mg, Pycnogenol 5 mg-2,000 mg, SAMe 10 mg-10000 mg, Cat's claw 1 mg-10000 mg, Boswellia serrata 1 mg-10000 mg, Stinging nettle 1 mg-20000 mg and Glutamine 1 mg-10000 mg for a treating chronic arthritis.

4. The micronutrient composition of claim 3, wherein the micronutrient composition decreases a pro-inflammatory IL-6 and secretion of matrix metalloproteinase 13, and/or the ECM damaging enzyme in a joint.

5. The micronutrient composition of claim 3, wherein the micronutrient composition is formulated as a capsule and is administered once a day, twice a day or three times a day.

6. A method of treating mammal suffering from a chronic arthritis, comprising:
   administering a micronutrient composition containing a Vitamin C 10 mg-50000 mg, Vitamin E (D-alpha tocopherol) 1 mcg-3000 mcg, Vitamin B6 0.1 mg-1000 mg, Vitamin D3 10 IU-10000 IU, Folic acid 10-5,000 mcg, L-proline 1 mg-20,000 mg, L-lysine 1 mcg-20000 mg, Copper 0.1 mg-15 mg, Betaine HCl 10 mg-2000 mg, Chondroitin sulfate 10 mg-10000 mg, N-acetyl-glucosamine 10 mg-50000 mg, Pycnogenol 5 mg-2,000 mg, SAMe 10 mg-10000 mg, Cat's claw 1 mg-10000 mg, Boswellia serrata 1 mg-10000 mg, Stinging nettle 1 mg-20000 mg and Glutamine 1 mg-10000 mg as specific dose.

7. The method of claim 6, further comprising:
   administering the said micronutrient composition for treating a joint related inflammation and reducing an ECM damaging enzymes in joints.

8. The micronutrient composition of claim 7, wherein the joint related inflammation is caused due to increased IL-6.

9. The method of claim 7, wherein the ECM damaging enzyme is matrix metalloproteinase 13.

10. The method of claim 6, wherein the specific dose is one oral capsule once a day, twice a day or three times a day.

* * * * *